(12) United States Patent
Miyazaki et al.

(10) Patent No.: US 11,712,582 B2
(45) Date of Patent: Aug. 1, 2023

(54) PATIENT POSITION DETERMINATION SYSTEM, METHOD, AND PROGRAM

(71) Applicant: Hitachi, Ltd., Tokyo (JP)

(72) Inventors: Koichi Miyazaki, Tokyo (JP); Toru Umekawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 161 days.

(21) Appl. No.: 17/601,454

(22) PCT Filed: Oct. 17, 2019

(86) PCT No.: PCT/JP2019/040787
§ 371 (c)(1),
(2) Date: Oct. 5, 2021

(87) PCT Pub. No.: WO2020/217569
PCT Pub. Date: Oct. 29, 2020

(65) Prior Publication Data
US 2022/0193453 A1      Jun. 23, 2022

(30) Foreign Application Priority Data

Apr. 26, 2019   (JP) .............................. JP2019-084817

(51) Int. Cl.
*A61N 5/10*           (2006.01)
*A61B 6/00*           (2006.01)
(52) U.S. Cl.
CPC .......... *A61N 5/1049* (2013.01); *A61B 6/4014* (2013.01); *A61B 6/487* (2013.01);
(Continued)

(58) Field of Classification Search
None
See application file for complete search history.

(56) References Cited

U.S. PATENT DOCUMENTS

2010/0246915 A1    9/2010   Yamakoshi et al.
2018/0137605 A1    5/2018   Otsuka et al.
(Continued)

FOREIGN PATENT DOCUMENTS

JP      2007-282877 A    11/2007
JP      2010-187991 A    9/2010
(Continued)

OTHER PUBLICATIONS

Long et al., "Fully Convolutional Networks for Semantic Segmentation", The CVPR2015 paper is the Open Access version, provided by the Computer Vision Foundation., The authoritative version of this paper is available in IEEE Xplore, pp. 3431-3440.
(Continued)

*Primary Examiner* — Hoon K Song
(74) *Attorney, Agent, or Firm* — Mattingly & Malur, PC

(57) ABSTRACT

A radiotherapy system includes X-ray imaging apparatuses that obtain an X-ray image of the patient on a reference plane, and a position determination apparatus. The position determination apparatus calculates parameters of a region estimation model, using, as input data, a reference fluoroscopic image obtained before radiotherapy, and also using, as teacher data, a reference ROI image obtained with respect to the reference fluoroscopic image before radiotherapy. During radiotherapy, the position determination apparatus estimates a region of interest with respect to the X-ray image and a DRR image, based on the parameters and the X-ray image, determines a degree of matching between the X-ray image and the DRR image for the region of interest while virtually changing a relative position/orientation relationship between a CT image and the reference plane, and determines an amount of deviation in position/orientation between the patient and the CT image.

14 Claims, 10 Drawing Sheets

(52) U.S. Cl.
    CPC ...... *A61N 5/1069* (2013.01); *A61N 2005/105* (2013.01); *A61N 2005/1061* (2013.01)

(56) References Cited

U.S. PATENT DOCUMENTS

| | | | |
|---|---|---|---|
| 2018/0154180 A1* | 6/2018 | Mori | .................. A61B 6/487 |
| 2018/0264288 A1 | 9/2018 | Sakata et al. | |
| 2018/0280727 A1* | 10/2018 | Takahashi | .............. G06T 11/005 |
| 2019/0060672 A1* | 2/2019 | Takahashi | .............. A61B 6/487 |
| 2020/0069967 A1 | 3/2020 | Mori et al. | |
| 2020/0155870 A1* | 5/2020 | Takahashi | ............ A61N 5/1067 |
| 2021/0038917 A1* | 2/2021 | Karasawa | ................. G06F 3/14 |

FOREIGN PATENT DOCUMENTS

| | | |
|---|---|---|
| JP | 2010-246883 A | 11/2010 |
| JP | 2013-99431 A | 5/2013 |
| JP | 2016-59606 A | 4/2016 |
| JP | 2018-0/1/86 A | 5/2018 |
| JP | 2018-89065 A | 6/2018 |
| JP | 2018-153299 A | 10/2018 |
| WO | 2018/083844 A1 | 5/2018 |

OTHER PUBLICATIONS

International Search Report of PCT/JP2019/040787 dated Dec. 17, 2019.

* cited by examiner

PATIENT POSITION DETERMINATION SYSTEM, METHOD, AND PROGRAM

TECHNICAL FIELD

The present invention relates to a patient position determination system, a patient position determination method, and a patient position determination program, and particularly relates to a technique for determining an amount of deviation in the position/orientation of a patient to be subjected to radiotherapy.

BACKGROUND ART

Radiotherapy is widely practiced, in which a target volume is irradiated with various kinds of radiant rays, which include such particle beams as X-rays and proton beams. When a treatment plan for radiotherapy is set up, a computed tomography (CT) image (three-dimensional image) of a patient is acquired in advance, and with respect to the patent, the irradiation position, irradiation direction, and the like of radiant rays are determined, based on the CT image. In general, irradiation of radiant rays in treatment is implemented at timing different from timing of treatment plan setting. To match the position/orientation of the patient at the time of CT image acquisition to the same at the time of performing treatment, therefore, patient position determination is essential.

In a process of patient position determination, an X-ray image of the patient lying on a couch is obtained on a reference plane defined on a radiotherapy system. In addition, a digital reconstructed radiography (DRR) image, which is created by projecting the CT image onto the reference plane, is obtained as a relative relationship in position/orientation (position/orientation relationship) between the CT image and the reference plane is changed. Based on a position/orientation relationship in which the X-ray image and the DRR image are approximate to or match each other, then, an amount of deviation in position/orientation of the couch is determined. Based on the amount of deviation in position/orientation obtained by such a position determination calculation, the position/orientation of the couch, that is, the position/orientation of the patient are fixed.

PTLs 1 and 2 listed below describe a technique of setting a region of interest with respect to an X-ray image, and determining, for the region of interest, a degree of matching between the X-ray image and a DRR image, thereby determining an amount of deviation in position/orientation of a couch. PTLs 1 and 2 describe, specifically, a technique of determining a position/orientation relationship in which the degree of matching exceeds a preset value while changing a position/orientation relationship between a space in which a CT image, from which the DRR image is constructed, is obtained and a reference plane on which the X-ray image is obtained, thereby determining the amount of deviation in position/orientation of the couch.

The region of interest is set at the time of determining the degree of matching between the X-ray image and the DRR image, and the degree of matching is determined for the set region of interest. This allows position determination with attention paid to a region (spine, pelvis, or the like) whose position does not change under the influence of the patient's respiration or heartbeat. FIG. 12 shows an example of an X-ray image and an ROI (region of interest) image that are obtained in a case where a target volume is on the chest. ROI is an abbreviation of "region of interest".

FIG. 12 shows an X-ray image 1201 taken from a place in front of a patient, an ROI image 1203 that is an image of an ROI set in accordance with the X-ray image 1201, and a superimposed image 1202 obtained by superimposing these images together. The ROI image 1203 is divided into two regions A and B. The region A represents a region set as the region of interest, and a region B represents a region not set as the region of interest. In the X-ray image of the chest, the position of the spine does not change under the influence of respiration or heartbeat. Thus, as shown in FIG. 12, by setting the region of interest as the spine, the amount of deviation in position/orientation of the patient is determined highly accurately and therefore highly accurate position determination is performed.

CITATION LIST

Patent Literature

PTL 1: JP 2007-282877 A
PTL 2: JP 2013-99431 A

Non-Patent Literature

NPL 1: Long, Jonathan, Evan Shelhamer, And Trevor Darrell. "Fully convolutional networks for semantic segmentation." Proc. of IEEE Conference on Computer Vision and Pattern Recognition (CVPR), 2015.

SUMMARY OF INVENTION

Technical Problem

The above-described conventional technique has the following problems. The user needs to set the region of interest, and therefore, depending on the technical proficiency of the user, the user has difficult in promptly carrying out a patient position determination calculation after taking the X-ray image. When the user fails to properly set the region of interest for such a reason that the user's technical proficiency is low, the correct amount of deviation in position/orientation cannot be calculated in some cases.

An object of the present invention is to quickly and accurately determine an amount of deviation in position/orientation of a patient with respect to a three-dimensional image of the patient that is obtained before radiotherapy.

Solution to Problem

The present invention provides a patient position determination system including an X-ray imaging apparatus that obtains an X-ray image of a patient on a reference plane, and an arithmetic processing apparatus. The arithmetic processing apparatus estimates a region of interest with respect to the X-ray image and to a DRR image, based on a parameter of a region estimation model and on the X-ray image or the DRR image created by virtually projecting a three-dimensional image of the patient obtained before radiotherapy onto the reference plane, and determines an amount of deviation in position/orientation between the patient and the three-dimensional image, based on the three-dimensional image, the X-ray image, and the region of interest. The parameter of the region estimation model is a parameter calculated by using, as input data, a reference fluoroscopic image obtained before radiotherapy, and also using, as teacher data, a reference ROI image obtained with respect to the reference fluoroscopic image before radiotherapy.

Advantageous Effects of Invention

According to the present invention, an amount of deviation in position/orientation between a three-dimensional image of a patient, which is obtained before radiotherapy, and the patient can be determined quickly and accurately.

DESCRIPTION OF EMBODIMENTS

A radiotherapy system according to each of embodiments of the present invention will hereinafter be described with reference to the drawings. The same matters depicted in a plurality of drawings are denoted by the same reference sings to avoid duplicated descriptions. A term "image" used in the specification herein means, in principle, image data to be subjected to arithmetic processing. When the term "image" specifically refers to an image to be taken or displayed, however, it means an image that can be actually or conceptually expressed on a two-dimensional plane.

Figure 1:
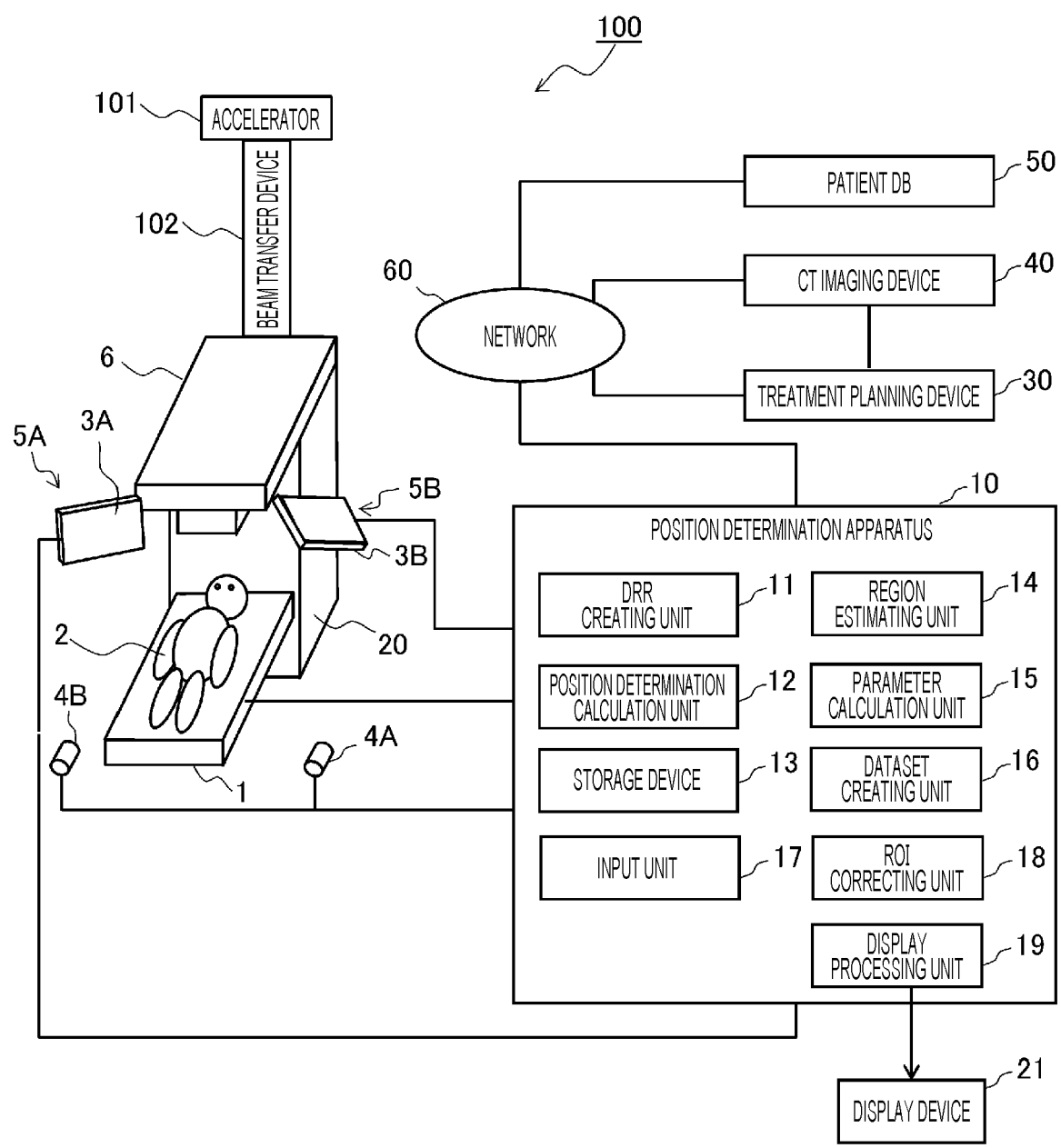
FIG. 1 is a diagram showing an overall schematic configuration of a patient position determination system.

FIG. 1 shows an overall schematic configuration of a radiotherapy system 100 according to a first embodiment of the present invention. The radiotherapy system 100 is a system that irradiates a target volume with radiant rays, the target volume being in a patient 2 on a couch 1. In each embodiment, an example of radiant rays being such heavy particle beams as carbon or helium beams or such particle beams as proton beams is shown. Radiant rays, however, are not limited to particle beams, and may be such photon beams as X-rays or y-rays. The radiotherapy system 100 includes constituent elements for particle beam irradiation, i.e., an accelerator 101, a beam transport device 102, and a particle irradiation device 6 that irradiates a target volume in the patient 2 with particle beams supplied from the accelerator 101.

The radiotherapy system 100 includes constituent elements involved in treatment plan setting, i.e., a treatment planning device 30, a CT imaging device 40, and a patient database (DB) 50. The CT imaging device 40 takes a CT image of the patient 2 in advance for treatment plan setting. The treatment planning device 30 sets a treatment plan, based on the image taken by the CT imaging device 40. The DB 50 stores information on the patient 2. It should be noted that although an example of using a CT image taken by the CT imaging device 40 is shown in each embodiment, a different three-dimensional image taken by a different imaging device, such as an MRI image taken by a magnetic resonance imaging (MRI) device or an ultrasonic image taken by an ultrasonic imaging device, may also be used.

The radiotherapy system 100 includes constituent elements involved in position determination calculation on the patient 2, i.e., X-ray imaging apparatuses 5A and 5B, a position determination apparatus 10, and a display device 21. The X-ray imaging apparatuses 5A and 5B take an X-ray image of the patient 2. The position determination apparatus 10 calculates an amount of deviation in position/orientation of the couch 1 and carries out a position determination calculation on the patient 2. The display device 21 displays an image corresponding to information outputted from the position determination apparatus 10.

The radiotherapy system 100 includes constituent elements for setting the position/orientation of the patient 2, i.e., the couch 1, and a couch driver 20 that drives the couch 1. Further, the radiotherapy system 100 includes a network 60 that interconnects various devices to allow them to communicate with each other.

Particle beams to be emitted on the patient 2 are accelerated by the accelerator 101 up to a necessary energy level, and are led by the beam transport device 102 to the particle irradiation device 6. The accelerator 101 may be a synchrotron accelerator, a cyclotron accelerator, or an accelerator different from these accelerators.

When X-rays are used in place of particle beams for treatment, a therapeutic X-ray irradiation device that generates therapeutic X-rays is provided in place of the accelerator 101 and the beam transport device 102. When g-rays are used, a y-ray irradiation device that generates therapeutic y-rays is provided in place of the accelerator 101 and the beam transport device 102.

The X-ray imaging apparatuses 5A and 5B include X-ray generators 4A and 4B that generate X-rays toward the patient 2, two-dimensional X-ray detectors 3A and 3B that detect two-dimensional dose distributions of the X-rays generated by the X-ray generators 4A and 4B and having passed through the patient 2, and a signal processing circuit (not illustrated).

The two-dimensional X-ray detectors 3A and 3B output analog signals from detection elements set in two-dimensional arrangement. The signal processing circuit processes the analog signals outputted from the two-dimensional X-ray detectors 3A and 3B to generate an X-ray image, and outputs the X-ray image to the position determination apparatus 10.

As the two-dimensional X-ray detectors 3A and 3B, for example, flat panel detectors (FPD) or image intensifiers (I.I) are used. Any two-dimensional detector capable of obtaining a two-dimensional image is applicable as the two-dimensional X-ray detectors 3A and 3B, and therefore two-dimensional detectors other than the FPD or I.I may also be provided as the two-dimensional X-ray detectors 3A and 3B.

In the present embodiment, the number of the X-ray imaging apparatuses is two, but is not limited thereto. Any number of the X-ray imaging apparatuses may be provided, providing that at least one X-ray imaging apparatus is provided. When an amount of deviation in position/orientation of the patient 2 at the time of taking an CT image and the same at the time of performing treatment are calculated with respect to three translatory displacement axes and three rotation axes, two or more X-ray imaging apparatuses may be used.

A virtual reference plane for position determination is defined in the radiotherapy system 100. The reference plane may be a plane on which X-ray images are taken by the X-ray imaging apparatuses 5A and 5B.

The position determination apparatus 10 includes a DRR creating unit 11, a position determination calculation unit 12, a storage device 13, a region estimating unit 14, a parameter calculation unit 15, a dataset creating unit 16, an input unit 17, an ROI correcting unit 18, and a display processing unit 19. The DRR creating unit 11 creates a DRR image by projecting a CT image onto the reference plane in virtual processing, that is, arithmetic processing. The position determination calculation unit 12 calculates an evaluation function, based on an X-ray image taken by the X-ray imaging apparatuses 5A and 5B, a DRR image, and an ROI image. Using the evaluation function, the position determination calculation unit 12 calculates an amount of deviation in position/orientation of the patient 2 at the time of performing treatment relative to the same at the time of taking the CT image.

The storage device 13 stores a dataset, which is a set of a reference fluoroscopic image and a reference ROI image. The region estimating unit 14 estimates a region of interest set for an X-ray image taken by the X-ray imaging apparatuses 5A and 5B. The parameter calculation unit 15 calculates a parameter of a region estimation model used by the region estimating unit 14, using a dataset stored in the storage device 13.

The dataset creating unit 16 creates a dataset, based on images obtained at the time of position determination on a patient treated in the past. The input unit 17 has interfaces, such as a mouse, a keyboard, and a switch, and inputs information to the position determination apparatus 10, accordance to a user's operation. The ROI correcting unit 18 corrects a region of interest estimated by the region estimating unit 14, according to the user's operation. The display processing unit 19 displays an X-ray image, a DRR image, and the like on the display device 21.

Processes executed by the constituent elements of the position determination apparatus 10 will be described specifically below. The DRR creating unit 11 reads a CT image taken by the CT imaging device 40 at the time of treatment plan setting, out of the patient DB 50, and virtually projects the CT image onto the reference plane, thereby creating a DRR image. Specifically, the DRR creating unit 11 sums up respective voxel values of the CT image along a virtual X-ray path to create the DRR image.

The position determination calculation unit 12 carries out a position determination calculation of calculating an amount of deviation in position/orientation between the CT image and the patient 2, based on a degree of matching between an X-ray image taken by the X-ray imaging apparatus 5A and 5B and the DRR image. Specifically, the DRR creating unit 11 creates the DRR image for evaluation, as the DRR image that is obtained when a geometric quantity related to at least either the translatory displacement and the rotation (which will hereinafter be referred to as "translatory displacement/rotation") of the CT image is virtually changed. The position determination calculation unit 12 calculates an evaluation function expressing a degree of matching between the DRR image for evaluation and the X-ray image.

The position determination calculation unit 12 calculates the amount of deviation in positional/orientation between the CT image and the patient 2, based on a relative position/orientation relationship between the CT image and the patient 2 that holds when the evaluation function satisfies a given condition. In other words, the position determination calculation unit 12 calculates the amount of deviation in positional/orientation between the CT image and the patient 2 ready for treatment, by determining the geometric quantity related to the translatory displacement/rotation so that the evaluation function takes a maximum value or exceeds a given threshold.

The evaluation function may be the absolute value of differences between pixel values of the DRR image for evaluation and pixel values of the X-ray image, mutual information volumes, mutual correlation coefficients, or the like. In addition, an optimization algorithm, such as a gradient method, may be adopted to determine the geometric quantity related to the translatory displacement/rotation. When calculating the evaluation function, the position determination calculation unit 12 sets a region of interest for the X-ray image and calculates the evaluation function in a range included in the region of interest. As a result, the amount of deviation in position/orientation of the patient 2 is calculated with attention paid to a region whose position does not change under the influence of the patient's respiration or heartbeat. In this manner, the position determination calculation unit 12 executes, for the region of interest, the position determination calculation based on the CT image and the X-ray image, thus calculating the amount of deviation in position/orientation between the CT image and the patient 2, based on the CT image, the X-ray image, and the region of interest.

The storage device 13 stores a set of a reference fluoroscopic image and a reference ROI image, as a dataset, thus constructing a database including one or a plurality of datasets. In this case, the storage device 13 stores, for example, an X-ray image that was obtained at the time of position determination on an unspecified patient treated in the past, and an ROI image representing a region of interest set for the X-ray image, as a reference fluoroscopic image and a reference ROI image, respectively.

Figure 2:
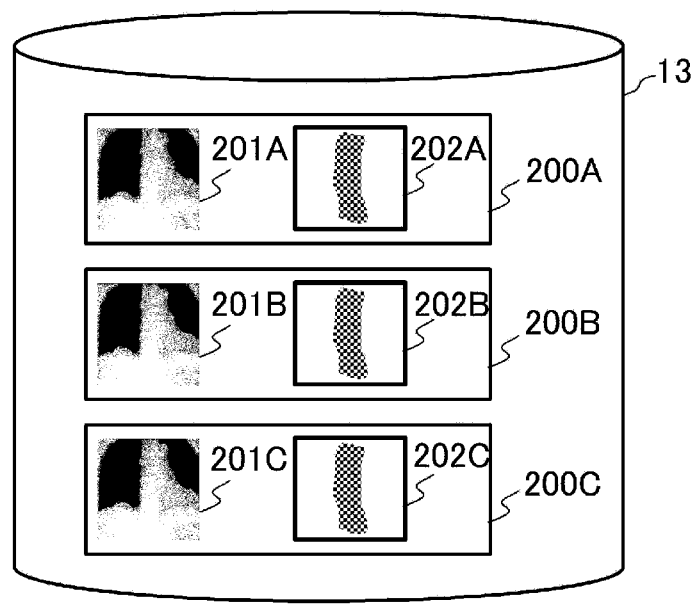
FIG. 2 is a conceptual diagram of a configuration of a database.

FIG. 2 is a conceptual diagram of a configuration of the database sored in the storage device 13. The storage device 13 stores datasets 200A, 200B, and 200C each consisting of sets of reference fluoroscopic images and reference ROI images. The reference fluoroscopic images and reference ROI images making up the dataset 200A include, for example, an X-ray image 201A and an ROI image 202A that were obtained at the time of position determination on the patient A treated in the past. Similarly, datasets 200B and 200C include, for example, X-ray images 201B and 201C and ROI images 202B and 202C, respectively, which were obtained at the time of position determination on patients B and C treated in the past. It should be noted that although FIG. 2 shows three datasets for simpler description, more datasets may be stored in the storage device 13 in actual cases.

The region estimating unit 14 carries out a region dividing process on a X-ray image of the patient 2, using a preset region estimation model and parameters calculated by the parameter calculation unit 15, and estimates an initial region of interest. As the region estimation model, a convolutional neural network (hereinafter "CNN") model as disclosed in NPL 1 may be used.

Figure 3:
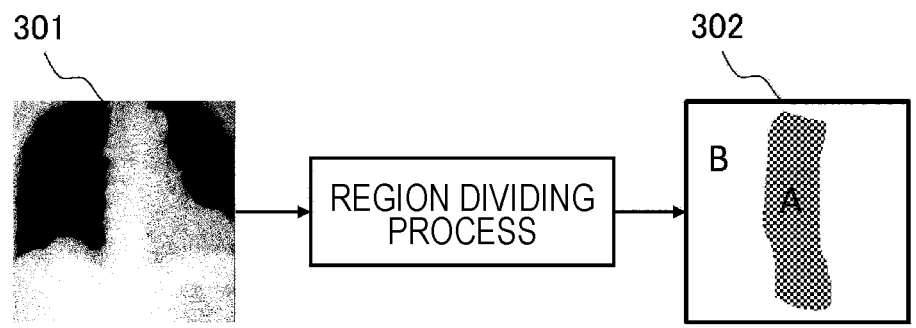
FIG. 3 is an explanatory diagram of an example of a region dividing process.

FIG. 3 is an explanatory diagram of an example of the region dividing process. For example, when a target volume is on the chest, the region estimating unit 14 carries out the region dividing process, using an X-ray image 301 of the chest as input data, and outputs an initial ROI image 302 as output data. The initial ROI image 302 is divided into two regions A and B, and the region A represents a region set as a region of interest while the region B represents a region not set as the region of interest.

The region estimation model is not limited to the model using the CNN. The region estimation model may be a model in which its parameters are learned using a reference fluoroscopic image as input data and a reference ROI image as teacher data. For example, a machine learning model different from the CNN model, such as support vector machine and random forest, may be used as the region estimation model.

The X-ray image 301 shown in FIG. 3 may be divided into three regions A, B, and C or more regions. In this case, the initial ROI image 302 is divided into the region A set as the region of interest, the region B not set as the region of interest, and the region C that is difficult to divide.

Using a dataset stored in the storage device 13, the parameter calculation unit 15 learns (calculates) parameters of a region division model used by the region estimating unit 14. When the CNN model is used as the region division model, an error function is determined, the error function getting smaller in value as the initial ROI image, which is outputted when the X-ray image is inputted, getting closer to an ideal ROI image. A parameter that minimizes the error function or makes it smaller than a given threshold is then calculated. As the error function, for example, a mean square error, a mean absolute value error, or the like may be used.

The input unit 17 receives operation information based on a user's operation, through such an interface as a mouse and a keyboard. The ROI correcting unit 18 corrects an ROI image, that is, corrects a region of interest, based on operation information inputted to the input unit 17. The display processing unit 19 displays an X-ray image, a DRR image, an ROI image, an amount of deviation in position/orientation obtained as a position determination calculation result, and the like, on the display device 21.

The position determination apparatus 10, the treatment planning device 30, and the like may be created by causing an arithmetic processing apparatus to execute a program. The arithmetic processing apparatus may be a computer equipped with a CPU, a memory, an interface, and the like, or a programmable arithmetic processing device, such as a field programmable gate array (FPGA). The program, which the arithmetic processing apparatus reads, is stored in an internal recording medium or an external recording medium (not illustrated), from which the program is read out by the arithmetic processing apparatus.

Operation commands to the position determination apparatus 10, the treatment planning device 30, and the like may be integrated into one program, or divided into a plurality of programs, or provided as a combination of one program and a plurality of programs. A part or all of the programs may be run on a dedicated hardware, or may be modularized. Furthermore, various programs delivered from a program distribution server, an internal storage medium, or an external recording medium may be installed in each of apparatuses/devices. The position determination apparatus 10, the treatment planning device 30, and the like do not need to be independent of each other, and two or more of apparatuses/devices may be integrated into a single form in which the apparatuses/devices carry out their share of processes.

Some of the plurality of constituent elements making up the position determination apparatus 10 may be configured by an external computer. The external computer may be directly connected to the position determination apparatus 10 or may be connected to a communication line, such as the Internet. Some or all of the plurality of constituent elements making up the position determination apparatus 10 may be individually configured by an electronic circuit, i.e., hardware.

As the storage device 13 included in the position determination apparatus 10, for example, a RAM, a ROM, a hard disk, a USB memory, an SD card, or the like may be used. The storage device 13 may be a storage on a communication line, such as the Internet. One constituent element included in the position determination apparatus 10 may be configured by a plurality of computers that execute distributed processing.

Figure 4:
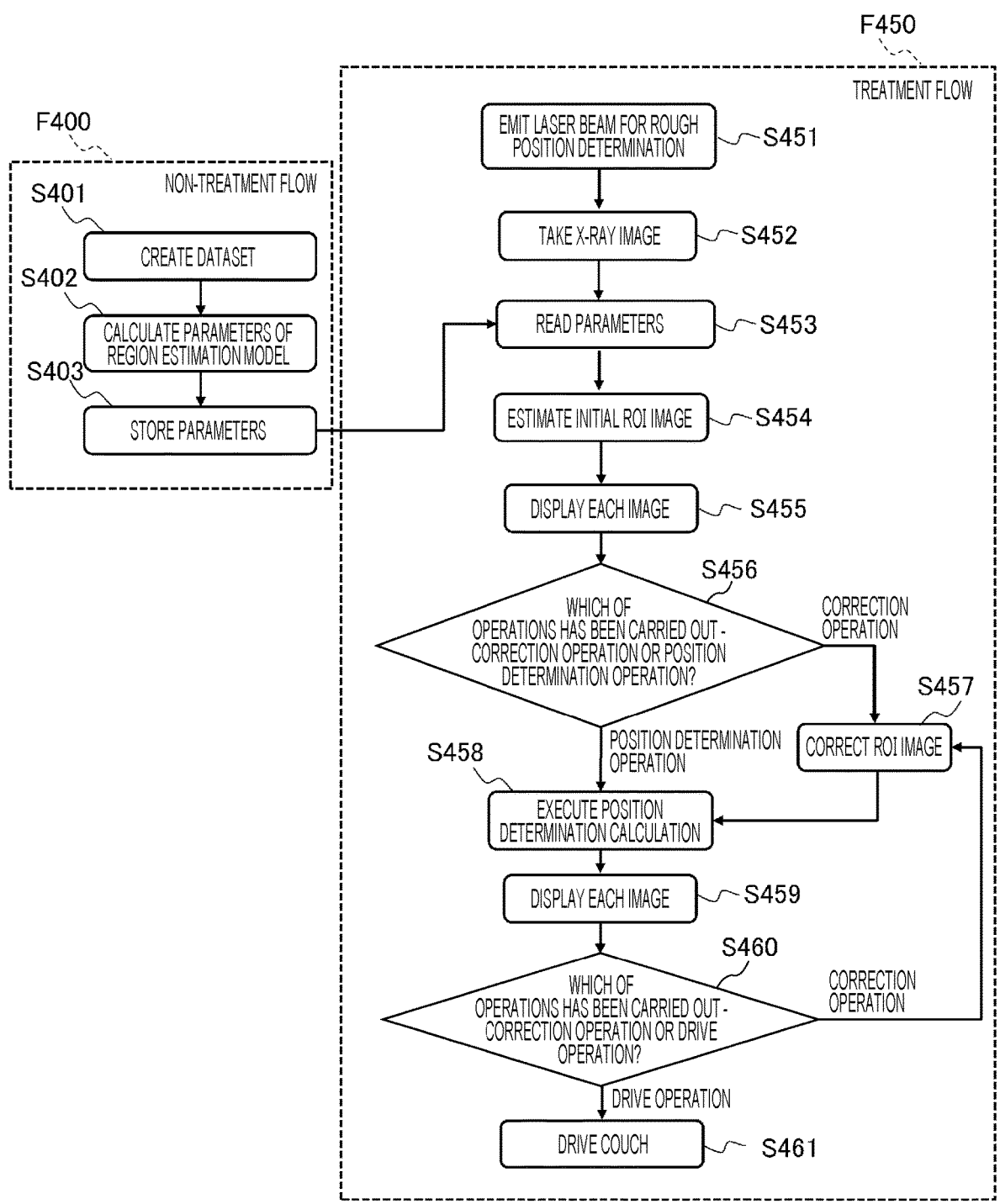
FIG. 4 is a flowchart showing a position determination procedure according to a first embodiment.

Details of processes executed by the radiotherapy system 100 according to the present embodiment will hereinafter be described. FIG. 4 is a flowchart showing a position determination procedure using the radiotherapy system 100 according to the present embodiment. This flowchart is divided into a non-treatment flow F400 executed at a time different from the time of treatment and a treatment flow F450 executed at the time of treatment.

In the non-treatment flow F400, the dataset creating unit 16 creates a dataset that is a set of a reference fluoroscopic image and a reference ROI image, and stores the dataset in the storage device 13 (S401). The reference fluoroscopic image and the reference ROI image that are prepared at this step may be, for example, an X-ray image and an ROI image that were obtained at the time of position determination on a patient treated in the past. The patient treated in the past may be one of unspecified patients including the patient 2 currently on treatment. Next, the parameter calculation unit 15 reads a dataset stored in the storage device 13, and calculates a parameter of a region estimation model (S402). The parameter calculation unit 15 then stores the calculated parameter in the storage device 13 (S403).

Subsequently, in the treatment flow F450, the patient 2 is laid on the couch 1. A laser marker (not illustrated) provided in the radiotherapy system 100 emits a laser beam for rough position determination onto the patient 2, according to an operation of the user who is engaging in treatment (S451). The user carries out rough position determination, referring to a laser exposure spot and a mark put on the patient 2. The X-ray imaging apparatuses 5A and 5B take an X-ray image (S452). Subsequently, the region estimating unit 14 reads parameters out of the storage device 13 (S453), and estimates an initial ROI image from the X-ray image obtained by the process of S452 (S454). The display processing unit 19 displays the X-ray image and the initial ROI image on the display device 21 (S455).

Referring to the X-ray image and ROI image displayed on the display device 21, the user judges whether correcting the ROI image is necessary. When judging that the estimation accuracy of the ROI image is low because of the number of datasets stored in the storage device 13 being insufficient and therefore correcting the ROI image is necessary, the user carries out a correction operation of correcting the ROI image on the input unit 17. When judging that correcting the ROI image is unnecessary, on the other hand, the user carries out a position determination operation on the input unit 17. The position determination operation is an operation of causing the position determination calculation unit 12 to execute a position determination calculation.

The ROI correcting unit 18 judges which of the correction operation and the position determination operation has been carried out on the input unit 17 (S456). When the correction operation has been carried out, the ROI correcting unit 18 corrects the ROI image according to the correction operation, and generates an ROI image having undergone the correction operation (corrected ROI image) (S457). When the ROI correcting unit 18 judges that the position determination operation has been carried out or when the correction of the ROI image is completed in the process of S457, the position determination calculation unit 12 executes a position determination calculation (S458).

After an amount of deviation in position/orientation is calculated by the position determination calculation, the display processing unit 19 displays the X-ray image, the DRR image, the ROI image from which the amount of deviation in position/orientation is determined, and the amount of deviation in position/orientation, on the display device 21 (S459). When these images are displayed, the position determination apparatus 10 corrects the region of interest according to the user's correction operation of correcting the region of interest, through the following process, and determines the amount of deviation in position/orientation for the corrected region of interest.

The user checks the X-ray image, the DRR image, the ROI image, and the amount of deviation in position/orientation that are displayed on the display device 21, and determines whether the amount of deviation in position/orientation has been determined properly.

When judging that the amount of deviation in position/orientation is not properly determined and therefore correcting the ROI image is necessary, the user carries out a correction operation of correcting the ROI image on the input unit 17. When judging that correcting the ROI image is unnecessary, on the other hand, the user carries out a drive operation on the input unit 17. The drive operation is an operation of causing the couch driver 20 to drive the couch 1.

The ROI correcting unit 18 judges which of the correction operation and the drive operation of driving the couch 1 has been carried out on the input unit 17 (S460). When the correction operation has been carried out, the ROI correcting unit 18 returns to the process of S457 and corrects the ROI image according to the correction operation (S457). When the ROI correcting unit 18 judges that the driving operation has been carried out at S458, the couch driver 20 drives the couch 1, based on the amount of deviation in position/orientation (geometric quantity related to translatory displacement/rotation) calculated by the position determination calculation (S461). As a result, the position/orientation of the patient 2 are fixed as the position/orientation for radiotherapy.

According to a conventional technique, after the X-ray imaging apparatus obtains an X-ray image, a region of interest is set by the user's operation. According to the present embodiment, in contrast, an ROI image is created, using a region estimation model set in advance, and a region of interest is set on the basis of this ROI image. This reduces a time spent on setting the region of interest, thus reducing a time spent on position determination on the patient.

According to the conventional technique, the position and range of the region of interest are set in a highly arbitrary manner, and properly setting the region of interest is difficult in some cases, depending on the technical proficiency of the user. According to the present embodiment, in contrast, the ROI image is generated from parameters of the region estimation model learned from the dataset. The region of interest is, therefore, set without depending on the technical proficiency of the user, and consequently the time spent on position determination on the patient is reduced.

Further, according to the present embodiment, the ROI image generated from parameters of the region estimation model is displayed and can be corrected by the user. After execution of the position determination calculation, the ROI image from which the amount of deviation in position/orientation is determined is displayed, and this ROI image can be corrected by the user. In this manner, even if the corrected ROI image obtained by arithmetic processing is improper, this ROI image is corrected by the user, based on the user's knowledge and experience, and therefore the position determination calculation is carried out highly accurately.

Figure 5:
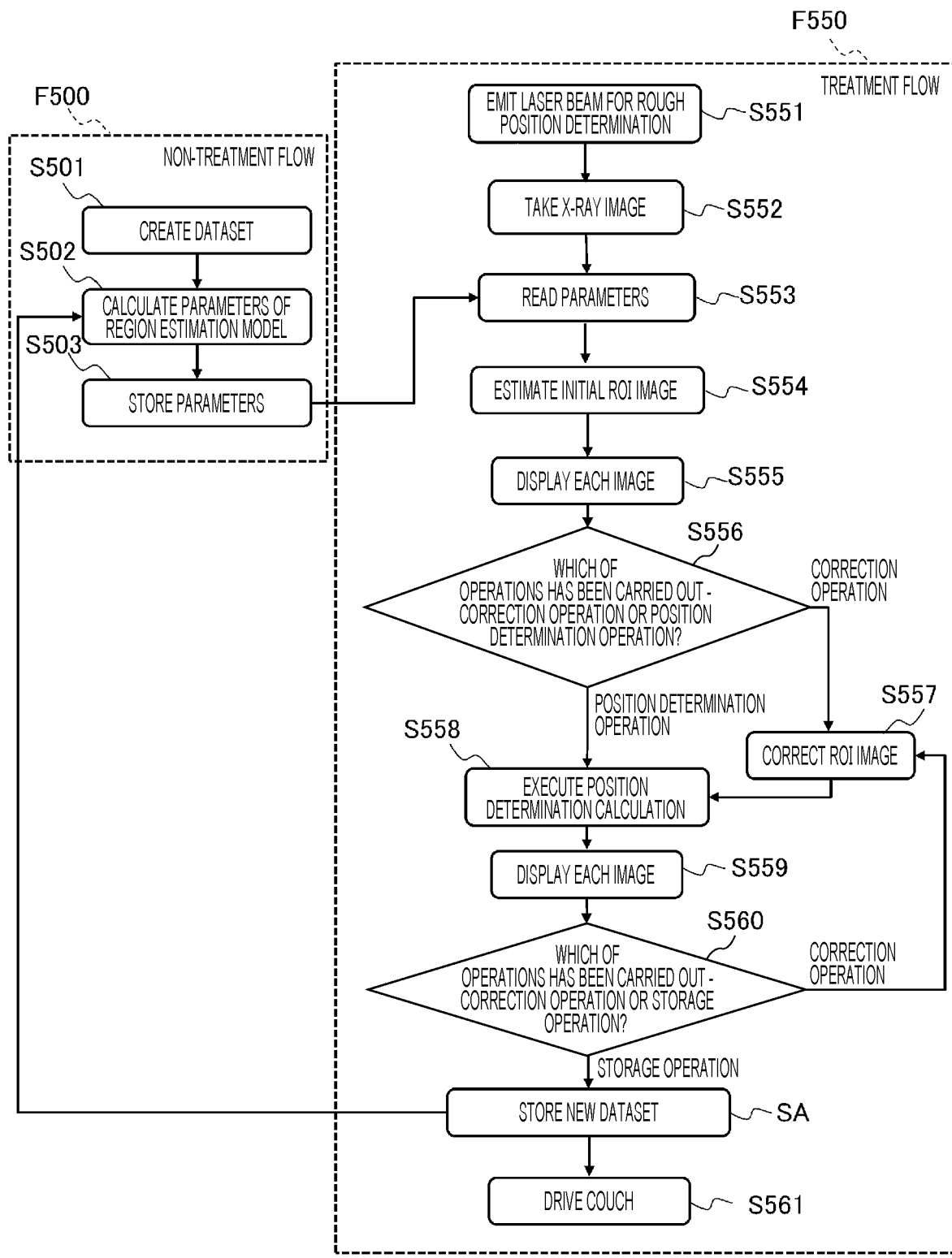
FIG. 5 is a flowchart showing a position determination procedure according to a second embodiment.
Figure 6:
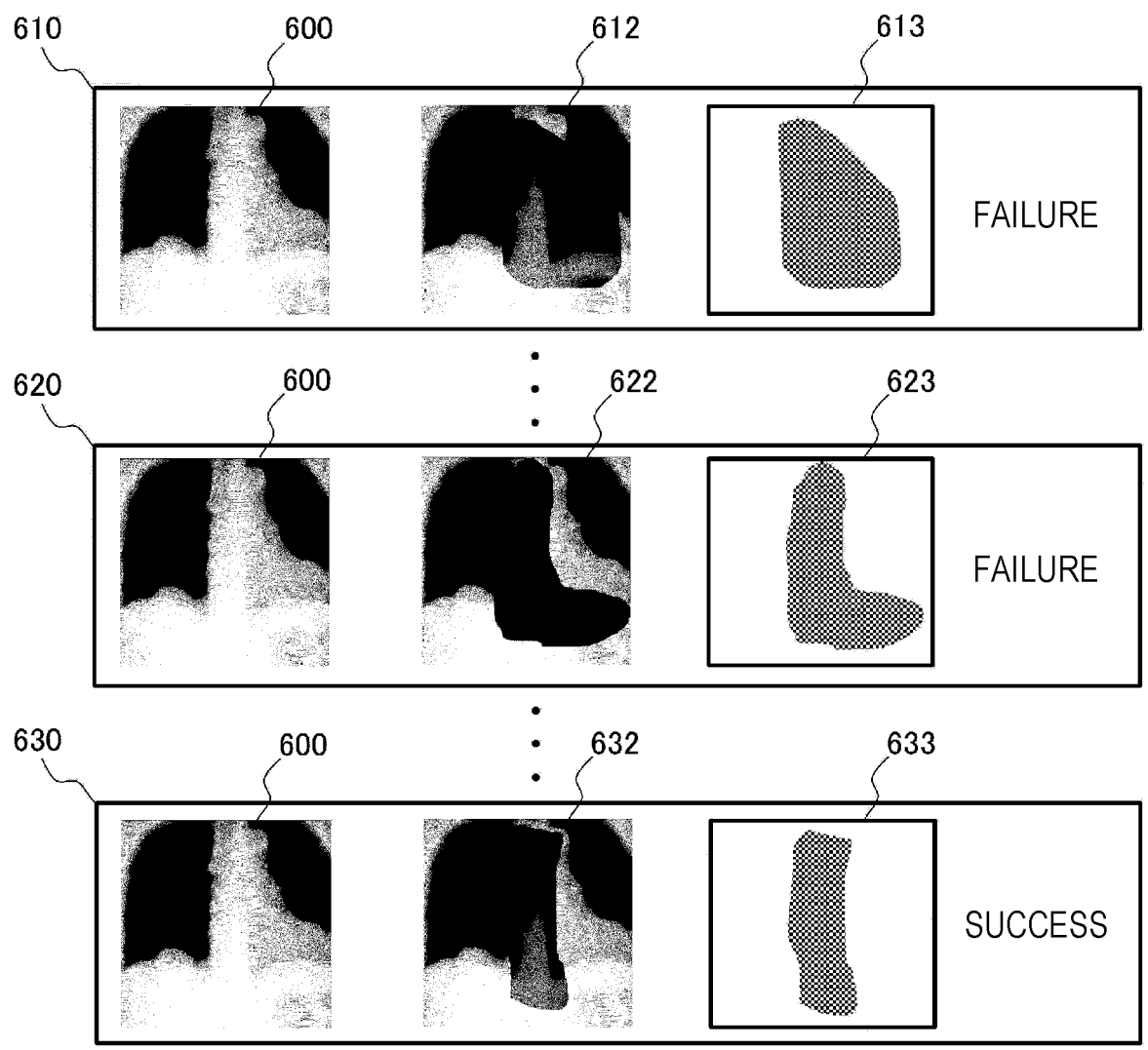
FIG. 6 is a conceptual diagram of a process of correcting a region of interest.

A second embodiment of the present invention will be described with reference to FIGS. 5 and 6. FIG. 5 is a flowchart showing a position determination procedure according to the second embodiment. FIG. 6 is a conceptual diagram of a process of correcting a region of interest according to the present embodiment.

In the present embodiment, every time position determination on the patient is carried out, an X-ray image and an ROI image that are obtained at the time of position determination are defined respectively as a new reference fluoroscopic image and a new reference ROI image. The new reference fluoroscopic image and the new reference ROI image are then additionally stored as a dataset, in the storage device 13, and parameters of the region estimation model are updated.

As shown in FIG. 5, a process flow for patient position determination is divided into a non-treatment flow F500 executed at a time different from the time of treatment and a treatment flow F550 executed at the time of treatment.

The non-treatment flow F500 is different from the non-treatment flow F400 shown in FIG. 4 in that the database to which a new dataset is added is used in a process of S502. Processes of S551 to S559 in the treatment flow F550 are the same as processes of S451 to S459 shown in FIG. 4.

After the process of S559, the user refers to an X-ray image, a DRR image, an ROI image from which an amount of deviation in position/orientation is determined, and the amount of deviation in position/orientation that are displayed on the display device 21, and judges whether correcting the ROI image is necessary. When judging that correcting the ROI image is necessary, the user carries out a correction operation of correcting the ROI image on the input unit 17. When determining that correcting the ROI image is unnecessary, on the other hand, the user carries out a dataset storage operation on the input unit 17. The dataset storage operation is an operation of causing the dataset creating unit 16 to store a new dataset in the storage device 13.

The ROI correcting unit 18 judges which of the correction operation and the dataset storage operation has been carried out on the input unit 17 (S560). When the correction operation has been carried out, the ROI correcting unit 18 returns to the process of S557 and corrects the ROI image according to the correction operation (S557).

When the ROI correcting unit 18 determines the dataset storage operation has been carried out at S560, the dataset creating unit 16 stores a new dataset in the storage device 13. Specifically, the dataset creating unit 16 defines the X-ray image and the finally generated ROI image as a reference fluoroscopic image and a reference ROI image, respectively, and stores a new dataset of these images in the storage device 13 (SA). In the process of S502, the parameter calculation unit 15 reads a previously stored dataset and a newly stored dataset as well, and calculates parameters of the region estimation model (S502).

After the process of SA is executed, the couch driver 20 drives the couch 1, based on the amount of deviation in position/orientation calculated by the position determination calculation (S561).

As described above, according to the present embodiment, every time the treatment flow F550 is executed, a new dataset is stored in the storage device 13, and the parameters of the region estimation model are updated. FIG. 6 is an explanatory diagram of a process in which the ROI correcting unit 18 corrects the ROI image and the dataset creating unit 16 stores a new dataset in the storage device 13. This diagram conceptually depicts a process of correcting the ROI image in a case of a target volume being on the chest.

An X-ray image 600, an initial ROI image 613, and a superimposed image 612 created by superimposing the X-ray image 600 and initial ROI image 613 together are shown as an initial image group 610. These images show a state in which an initial region of interest includes not only the spinal region but also the cardiac region and the diaphragmatic region for such a reason that the number of datasets stored in the storage device 13 is insufficient. When a position determination calculation is carried out using the initial ROI image 613, therefore, the calculation may possibly turn out to be improper one. In this case, the user corrects the ROI image according to processes of S556, S560, and S557.

FIG. 6 shows the X-ray image 600, a corrected ROI image 623, and a superimposed image 622 created by superimposing the X-ray image 600 and corrected ROI image 623 together, as an image group 620 corrected i times. These images show a state in which the region of interest includes the diaphragmatic region. In this case, the position determination calculation may possibly end up in a failure. FIG. 6 shows also the X-ray image 600, a corrected ROI image 633, and a superimposed image 632 created by superimposing the X-ray image 600 and corrected ROI image 633 together, as an image group 630 corrected n times. These images show a state in which the region of interest is limited to the spinal region. This case gives a possibility that the position determination calculation is successful.

In the above-described example, the ROI image 633 is an ROI image that should preferably be estimated from the region estimation model. However, an ROI image actually estimated from the region estimation model is the initial ROI image 613. In the present embodiment, following correction of the ROI image, the X-ray image 600 and the ROI image 633 obtained as a result of successful position determination are defined as a reference fluoroscopic image and a reference ROI image, respectively, and a new dataset of these images is stored in the storage device 13. Hence, parameters of a region estimation model giving a possibility of the ROI image 633 being estimated with respect to the X-ray image 600 are determined.

According to the present embodiment, the accuracy of estimation of the ROI image, using the region estimation model, is improved. In addition, as the number of treated patients increases and consequently the number of datasets included in the database increases, the ability in generalization of the region estimation model improves, which leads to an improvement in the accuracy of estimation of the ROI image with respect to the X-ray image of a new patient. As a result, the user is more frequently saved his or her trouble of correcting the initial ROI image, which provides a possibility that the time required for position determination on the patient is further reduced.

Figure 7:
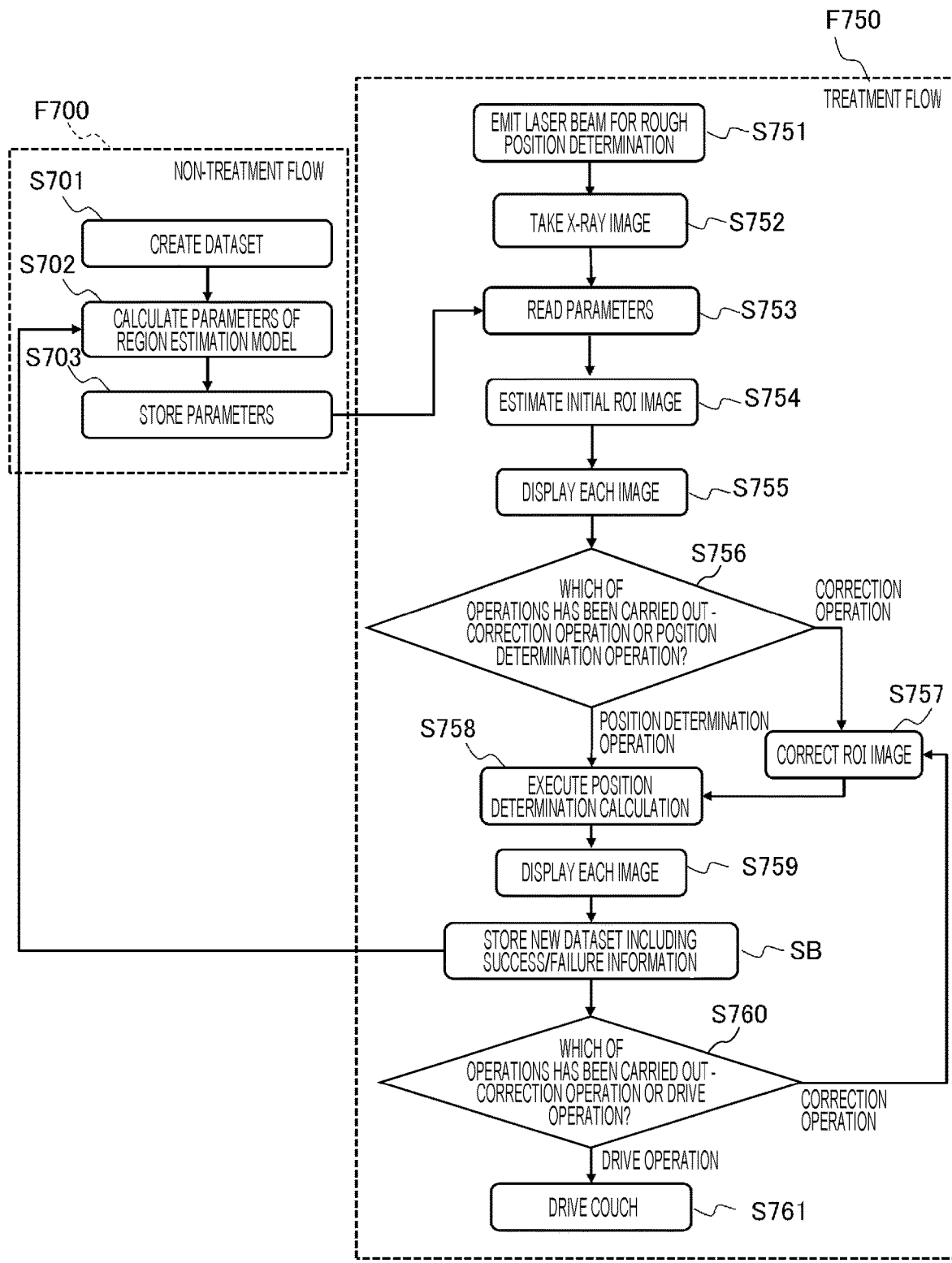
FIG. 7 is a flowchart showing a position determination procedure according to a third embodiment.
Figure 8:
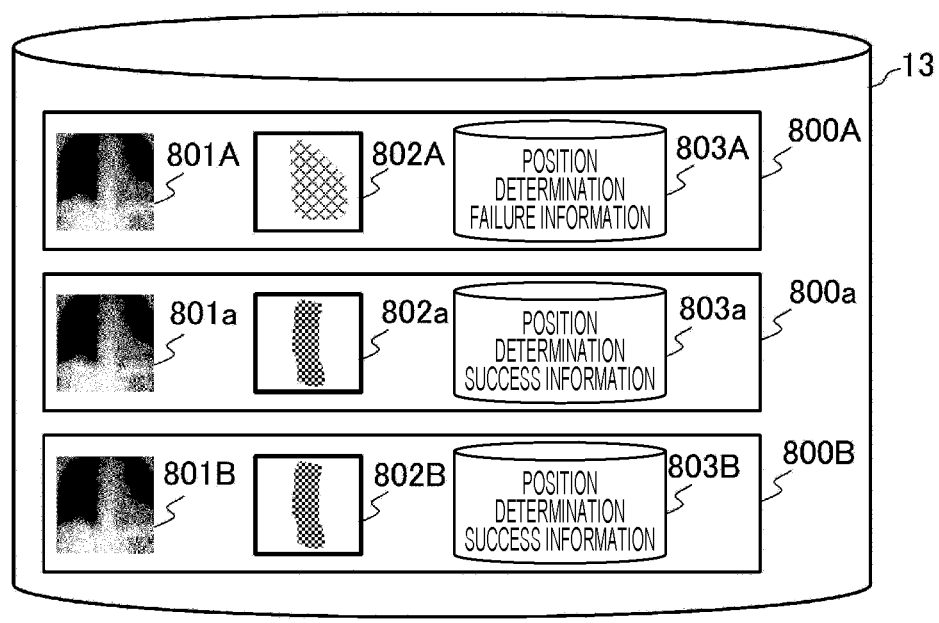
FIG. 8 is a conceptual diagram of a configuration of the database.
Figure 9:
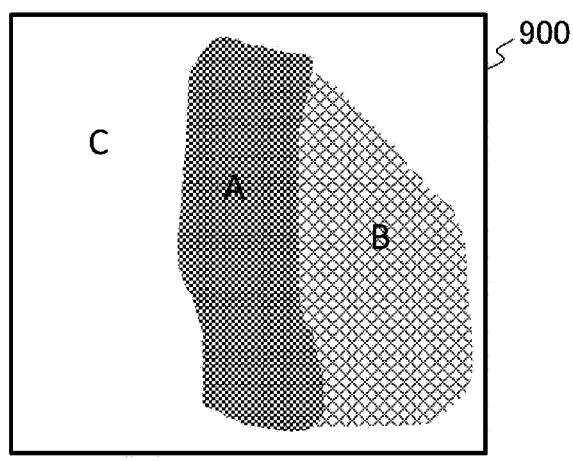
FIG. 9 is a conceptual diagram of a learning data creating method carried out by a parameter calculating unit.

A third embodiment of the present invention will be described with reference to FIGS. 7 to 9. FIG. 7 is a flowchart showing a position determination procedure according to the third embodiment. FIG. 8 conceptually depicts a configuration of datasets according to the present embodiment. FIG. 9 conceptually depicts a learning data creating method according to the present embodiment, the method being executed by the parameter calculation unit 15.

In the present embodiment, an X-ray image and an ROI image that are obtained at the time of position determination are defined as a reference fluoroscopic image and a reference ROI image, respectively. In addition, a dataset consisting of a set of the reference fluoroscopic image, the reference ROI image, and position determination success/failure information is additionally stored in the storage device 13, and parameters of a region estimation model is updated. The position determination success/failure information, which will be described later, is information indicating whether a position determination calculation has succeeded or failed.

The flowchart shown in FIG. 7 is divided into a non-treatment flow F700 executed at a time different from the time of treatment and a treatment flow F750 executed at the time of treatment. The non-treatment flow F700 is different from the non-treatment flow F400 shown in FIG. 4 in that the database to which a new dataset is added is used at S702.

Processes of S751 to S761 in the treatment flow F750 are the same as processes of S451 to S461 shown in FIG. 4. The treatment flow F750 is different from the treatment flow S450 shown in FIG. 4 in that a process of storing a new dataset including the position determination success/failure information in the storage device 13 is inserted between a process of S759 and a process of S760.

After the process of S759, the user refers to an X-ray image, a DRR image, a ROI image from which an amount of deviation in position/orientation is determined, and the amount of deviation in position/orientation that are displayed on the display device 21, and judges whether a position determination calculation has succeeded.

When judging that the position determination calculation has failed, the user carries out a calculation-failure storage operation on the input unit 17, and then carries out a correction operation of correcting the ROI image.

The calculation-failure storage operation is an operation of causing the dataset creating unit 16 to execute a process of storing a new dataset. The new dataset includes position determination success/failure information (position determination failure information) indicating a failure in the position determination calculation. By this calculation-failure storage operation, an X-ray fluoroscopic image and an ROI image, which are specified as images to be displayed, are defined as a new reference fluoroscopic image and a new reference ROI image, respectively. A dataset including the position determination failure information, in addition to the reference fluoroscopic image and the reference ROI image, is then stored in the storage device 13.

When judging that the position determination calculation has succeeded, the user carries out a calculation-success storage operation on the input unit 17, and then carries out the drive operation.

The calculation-success storage operation is an operation of causing the dataset creating unit 16 to execute a process of storing a new dataset. The new dataset includes position determination success/failure information (position determination success information) indicating a success in the position determination calculation. By this calculation-failure storage operation, an X-ray fluoroscopic image and an ROI image, which are specified as images to be displayed, are defined as a new reference fluoroscopic image and a new reference ROI image, respectively. A dataset including the position determination success information, in addition to the reference fluoroscopic image and the reference ROI image, is then stored in the storage device 13.

The dataset creating unit 16 executes a process of storing the new dataset including the position determination success/failure information, according to the calculation-failure storage operation or the calculation-success storage operation carried out by the user following the process of S759 (SB). The process of S760 is executed in response to the correction operation or the drive operation carried out following the calculation-failure storage operation or the calculation-success storage operation. The process of S760 executed in response to the correction operation or the drive operation is the same as the process of S460.

When the dataset creating unit 16 stores the dataset in the storage device 13 by the process of SB, the parameter calculation unit 15 calculates parameters of the region estimation model, based on a previously stored dataset and on the newly stored dataset as well (S702). In this case, the parameter calculation unit 15 calculates the parameters of the region estimation model, using, as input data, the reference fluoroscopic image and using also, as teacher data, the position determination success/failure information as well as the reference ROI image. In other words, the parameter calculation unit 15 calculates the parameters by an algorithm that reflects whether a reference region of interest image has brought a success in the position determination calculation or a failure in the same. This improves the accuracy of calculation of the parameters of the region estimation model. The parameter calculation unit 15 stores the calculated parameters in the storage device 13 (S703).

FIG. 8 conceptually depicts the database stored in the storage device 13 according to the present embodiment. The storage device 13 stores datasets 800A, 800*a*, and 800B each consisting of a set of a reference fluoroscopic image, a reference ROI image, and position determination success/failure information.

The dataset 800A is made up of, for example, an X-ray image 801A, an ROI image 802A, and position determination failure information 803A that were used when the first round of position determination calculation was carried out on a patient A treated in the past and ended up in a failure. The dataset 800*a* is made up of an X-ray image 801*a*, an ROI image 802*a*, and position determination success information 803*a* that were used when the second round of position determination calculation was carried out on the same patient A indicated in the dataset 800A and was successful. Similarly, the dataset 800B is made up of an X-ray image 801B, an ROI image 802B, and position determination success information 803B that were used when the first round of position determination calculation was carried out on a patient B treated in the past and was successful.

The position determination success/failure information (position determination success information and position determination failure information) may be of any given form, providing that such a form indicates whether the position determination calculation has succeeded or failed. For example, the number "1" may be assigned to the information indicative of success, and the number "0" may be assigned to the information indicative of failure. In another case, the information may take the form of text data composed of character codes, such as "success" and "failure". It should be noted that although FIG. 8 shows three datasets for simpler description, more datasets may be stored in the storage device 13 in actual cases.

As described above, when the position determination success/failure information is stored together with the reference fluoroscopic image and the reference ROI image, information for succeeding in the position determination calculation is provided to the user by the following display process.

For example, when the parameters are learned using the ROI image 802A of FIG. 8 that has led to a failure in the position determination calculation and the ROI image 802*a* of FIG. 8 that has led to a success in the position determination calculation, an ROI correction process image 900 is created from the ROI image 802A and the ROI image 802*a*, as shown in FIG. 9. The ROI correction process image includes three regions A, B, and C. The region A represents an ROI region having been set as the region of interest when the position determination calculation is successful. The region B represents a region having been set, together with the region A, as the region of interest when the position determination calculation fails. A region C represents a region having been not set as the region of interest.

It is assumed in this case that setting the region B as the region of interest results in a drop in the accuracy of position determination. By learning the parameters using the X-ray image and the ROI correction process image, therefore, the region A set as the region of interest and the region C not set as the region of interest, plus the region B that leads to a drop in the position determination accuracy when set as the region of interest, are estimated. At the time of position determination, the display processing unit 19 may display the region B on the display device 21. This gives the user a warning against use of the region B as the region of interest, thus increasing the possibility of a success in the position determination calculation.

In addition, in a case where the user's technical proficiency is low, a region that leads to a drop in the position determination accuracy when set as the region of interest may be displayed on the display device 21. This allows the user to easily visually recognize a region that should be set as the region of interest, thus quickly improving the user's technical proficiency.

Figure 10:
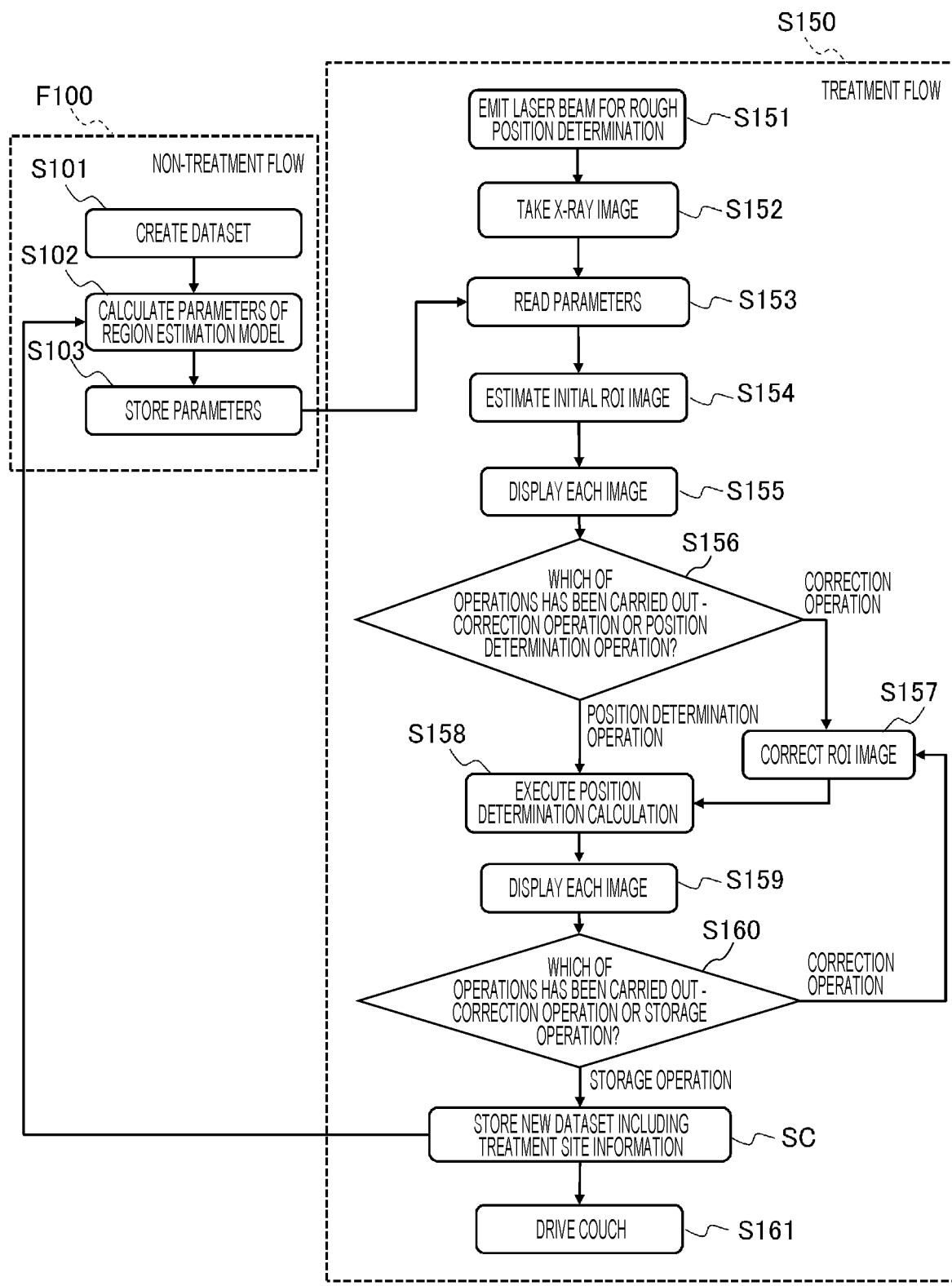
FIG. 10 is a flowchart showing a position determination procedure according to a fourth embodiment.
Figure 11:
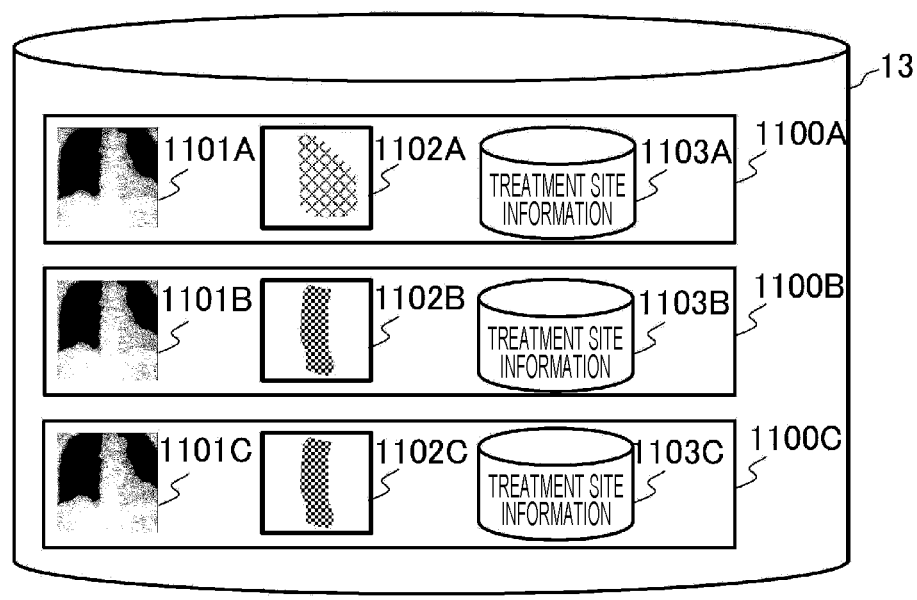
FIG. 11 is a conceptual diagram of a configuration of the database.
Figure 12:
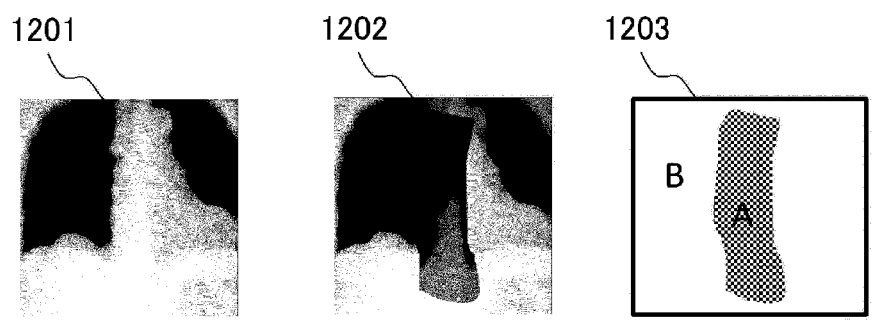
FIG. 12 is a diagram showing an example of an X-ray image and an ROI image.

A fourth embodiment of the present invention will be described with reference to FIGS. 10 and 11. FIG. 10 is a flowchart showing a process procedure according to the fourth embodiment. FIG. 11 conceptually depicts a database according to the present embodiment.

In the present embodiment, an X-ray image and an ROI image that are obtained at the time of position determination are defined as a new reference fluoroscopic image and a new reference ROI image, respectively. In addition, a dataset consisting of a set of the reference fluoroscopic image, the reference ROI image, and treatment site information is additionally stored in the storage device 13, and parameters of a region estimation model is updated. The treatment site information is information indicating a site to be treated. The treatment site information may be a numerical value or the like assigned in advance to the site to be treated.

The flowchart shown in FIG. 10 is divided into a non-treatment flow F100 executed at a time different from the time of treatment and a treatment flow F150 executed at the time of treatment.

A process of S101 in the non-treatment flow F100 is the same as the process of S501 shown in FIG. 5. Processes of S102 and S103 are different from the processes of S502 and S503 shown in FIG. 5 in that the processes of S102 and S103 are executed on the treatment site indicated by the treatment site information, which will be described later. Processes of S151 to S159 in the non-treatment flow F150 are the same as the processes of S551 to S559 in the non-treatment flow shown in FIG. 5, respectively.

After the process of S159, the user refers to an X-ray image, a DRR image, a ROI image from which an amount of deviation in position/orientation is determined, and the amount of deviation in position/orientation that are displayed on the display device 21, and judges whether correcting the ROI image is necessary. When judging that correcting the ROI image is necessary, the user carries out a correction operation of correcting the ROI image on the input unit 17. When determining that correcting the ROI image is unnecessary, on the other hand, the user carries out a dataset storage operation on the input unit 17. The storage operation is an operation of inputting treatment site information to the dataset creating unit 16 and causing the dataset creating unit 16 to store a new dataset in the storage device 13.

The ROI correcting unit 18 judges which of the correction operation and the storage operation has been carried out on the input unit 17 (S160). When the correction operation has been carried out, the ROI correcting unit 18 returns to the process of S157 and corrects the ROI image according to the correction operation (S157). When the ROI correcting unit 18 judges that the storage operation has been carried out at S160, the dataset creating unit 16 reads the treatment site information, and at the same time, creates a new dataset and stores it in the storage device 13 (SC).

The new dataset includes the treatment site information. By the process executed by the dataset creating unit 16, an X-ray image and an ROI image, which are specified as images to be displayed, are defined as a new reference fluoroscopic image and a new reference ROI image, respectively. A dataset including the treatment site information, in addition to the reference fluoroscopic image and the reference ROI image, is then stored in the storage device 13.

After this process of SC is executed, the couch driver 20 drives the couch 1, based on the amount of deviation in position/orientation calculated by the position determination calculation (S161).

When the dataset creating unit 16 stores the dataset in the storage device 13 by the process of SC, the parameter calculation unit 15 calculates parameters of a region estimation model for the treatment site indicated by the treatment site information included in the dataset (S102). The parameter calculation unit 15 associates the parameters with the treatment site information and stores the parameters in the storage device 13 (S103).

The treatment site information may be specified in a treatment plan. In this case, in the processing of S153, the region estimating unit 14 reads the parameters corresponding to the treatment site information indicated in the treatment plan.

FIG. 11 conceptually depicts the database stored in the storage device 13. The storage device 13 stores datasets 1100A, 1100B, and 1100C each consisting of a set of a reference fluoroscopic image, a reference ROI image, and treatment site information. The dataset 1100A is made up of, for example, an X-ray image 1101A, an ROI image 1102A, and treatment site information 1103A that were obtained at the time of position determination on the patient A treated in the past. Similarly, the datasets 1100B and 1100C are made up of, for example, X-ray images 1101B and 1101C, ROI images 1102B and 1102C, and treatment site information 1103B and 1103C, respectively, which were used at the time of position determination on patients B and C.

The treatment site information may be of any given form, providing that such a form tells the user where the target volume is. For example, when the target volume is the chest, the number "0" may be assigned to the information, when the target volume is the prostate, the number "1" may be assigned, and when the target volume is the head and neck, the number may be assigned. The treatment site information may be text data indicating the treatment site, such as "chest", "prostate", "head and neck". It should be noted that although FIG. 11 shows three datasets for simpler description, more datasets may be stored in the storage device 13 in actual cases.

Generally, the region of interest set on the basis of the X-ray image varies, depending on the treatment site. Classifying a plurality of datasets stored in the storage device 13, based on the treatment site, therefore, facilitates a process of reading a necessary dataset according to the treatment site. According to the present embodiment, in addition to the reference fluoroscopic image and the reference ROI image, the treatment site information is stored in the storage device 13. This facilitates a process of reading the dataset corresponding to the treatment site, thus allowing parameters of the region estimation model corresponding to the treatment site to be calculated quickly.

The processes of SA, SB, and SC shown respectively in FIGS. 5, 7, and 10, that is, the process of storing the dataset in the storage device 13 may be carried out only on the image selected by the user's operation. Specifically, the user refers to information displayed on the display device 21 by the processes of S559, S759, or S159, and judges whether or not to store the X-ray image and the ROI image from which the amount of deviation in position/orientation is determined, as a new dataset.

When judging that it is OK to store these images as the new dataset, the user carries out a storage operation for executing the processes of S559, S759, or S159, on the input unit 17. When judging that it is not OK to store these images as the new dataset, the user carries out a skip operation for skipping the processes of S559, S759, or S159, on the input unit 17.

The position determination apparatus 10 causes the storage device 13 to store the dataset in accordance with the user's operation that is carried out when the display device 21 displays the X-ray image, the DRR image, the ROI image from which the amount of deviation in position/orientation is determined, and the amount of deviation in position/orientation. In other words, the dataset creating unit 16 executes the processes of SA, SB, or SC in response to the storage operation being carried out on the input unit 17. In response to the skip operation being carried out on the input unit 17, the position determination apparatus 10 does not execute the process of storing the new dataset (SA, SB, SC) and executes the next process (S561, S760, S161), instead.

According to the above process flow, the user confirms that the ROI image from which the amount of deviation in position/orientation is determined is proper, based on the user's knowledge and experience, and then the ROI image from which the amount of deviation in position/orientation is determined is reflected in the database. In this manner, the properness of the ROI image, the properness being difficult to judge by arithmetic processing, is judged by the user, and the parameters of the region estimation model are determined highly accurately.

The dataset creating unit 16 may judge whether or not to store a new dataset according to the number of times of execution of the ROI image correction processes (S557, S757, S157). For example, the dataset creating unit 16 may execute the process of storing the new dataset only when the ROI image correction processes has not been executed. In another case, the dataset creating unit 16 may execute the process of storing the new dataset only when the number of times of execution of the ROI image correction processes is equal to or smaller than a preset number of times.

When judging that the new dataset is to be stored, the dataset creating unit 16 stores the new dataset in the storage device 13 according to the user's storage operation. When judging that the new dataset is not to be set, on the other hand, the dataset creating unit 16 does not carry out the process of storing the new data set (SA, SB, SC) even if the user has carried out the storage operation. Following this, the position determination apparatus 10 executes the next process (S561, S760, S161).

In the process of determining the ROI image, a fewer number of times of correction of the ROI image makes the finally determined ROI image more proper in some cases. In such a case, a new dataset is stored only when the number of times of correction satisfies a given condition, so that a proper ROI image is reflected in the database.

The embodiments according to which the region of interest is set in the X-ray image has been described above. The region of interest, however, may be set in the DRR image. In this case, in place of the X-ray image as a reference image, the DRR image as a reference image is set as the reference fluoroscopic image. The storage device 13 thus stores a dataset in which a DRR image obtained in the past is set as a reference fluoroscopic image.

Accordingly, at S452 in FIG. 4, in place of the process of taking an X-ray image by the X-ray imaging apparatuses 5A and 5B, the process of creating a DRR image by the DRR creating unit 11 is executed. At S454, in place of the process of estimating an initial ROI image from the X-ray image using parameters of a region estimation model, the process of estimating the initial ROI image from the DRR image using the parameters of the region estimation model is executed. In the process of S455, the X-ray image and the initial ROI image are not displayed on the display device 21, and the DRR image and the initial ROI image are displayed on the display device 21, instead.

The processes of S552, S554, and S555 in FIG. 5, the processes of S752, S754, and S755 in FIG. 7, and the processes of S152, S154, and S155 in FIG. 10 are replaced respectively with the processes using the DRR image as the reference fluoroscopic image, in the same manner as described above.

The radiotherapy system 100 according to each embodiment uses a method including the following steps (i) to (vi). The position determination apparatus 10 may execute a program for executing the following steps (iv) to (vi).

(i) Obtaining a reference fluoroscopic image of the patient 2 before implementation of radiotherapy. (ii) Obtaining a reference ROI image with respect to the reference fluoroscopic image before implementation of radiotherapy. (iii) Calculating parameters of a region estimation model, using the reference fluoroscopic image as input data and the reference ROI image as teacher data. (iv) Obtaining an X-ray image of the patient 2 on the reference plane by the X-ray imaging apparatus 5A and 5B. (v) Estimating a region of interest for the X-ray image and the DRR image, based on the parameters and on the X-ray image or DRR image. (vi) Determining an amount of deviation in position/orientation between the patient 2 and a three-dimensional image, based on the three-dimensional image, the X-ray image, and the region of interest. (vii) Causing the couch driver 20 to set the position/orientation of the couch 1 bearing the patient 2 laying thereon, based on the amount of deviation in position/orientation.

The position determination calculation described in the above step (vi) may be executed in accordance with the following steps. (vi-1) Determining a DRR image for evaluation as a DRR image that results when a relative position/orientation relationship between the three-dimensional image and the reference plane is virtually changed, and determining, for the region of interest, a degree of matching between the X-ray image and the DRR image for evaluation. (vi-2) Determining the amount of deviation in position/orientation between the patient 2 and the three-dimensional image, based on the position/orientation relationship that is held when the degree of matching satisfies a given condition.

REFERENCE SIGNS LIST

1 couch
2 patient
3A, 3B two-dimensional X-ray detector
4A, 4B X-ray generator
5A, 5B X-ray imaging apparatus
6 particle irradiation device
10 position determination apparatus
11 DRR creating unit
12 position determination calculation unit
13 storage device
14 region estimating unit
15 parameter calculation unit
16 dataset creating unit
17 input unit
18 ROI correcting unit
19 display processing unit
20 couch driver
21 display device
30 treatment planning device
40 CT imaging device
50 patient DB
60 network
100 radiotherapy system
101 accelerator
102 beam transport device
200A, 200B, 200C, 800A, 800B, 800C, 1100A, 1100B, 1100C dataset
201A, 201B, 201C, 301, 600, 801A, 801a, 801B, 1101A, 1101B, 1101C, 1201 X-ray image
302 initial ROI image
610 initial image group
612, 622, 632, 1202 superimposed image
613 initial ROI image
620 image group having undergone i rounds of correction
202A, 202B, 202C623, 633, 802A, 802a, 802B, 1102A, 1102B, 1102C, 1203 ROI image
630 image group having undergone n rounds of correction
633 ROI image having undergone N rounds of correction
803A position determination failure information
803a, 803B position determination success information
900 ROI correction process image
1103A, 1103B, 1103C treatment site information

The invention claimed is:
1. A patient position determination system comprising:
an X-ray imaging apparatus that obtains an X-ray image of a patient on a reference plane; and
an arithmetic processing apparatus, wherein the arithmetic processing apparatus estimates a region of interest with respect to the X-ray image and to a DRR image, based on a parameter of a region estimation model and on the X-ray image or the DRR image created by virtually projecting a three-dimensional image of the patient obtained before radiotherapy onto the reference plane, and obtains an amount of deviation in position/orientation between the patient and the three-dimensional image, based on the three-dimensional image, the X-ray image, and the region of interest, and wherein the parameter of the region estimation model is a parameter calculated by using, as input data, a reference fluoroscopic image obtained before radiotherapy, and also using, as teacher data, a reference ROI image obtained with respect to the reference fluoroscopic image before radiotherapy.

2. The patient position determination system according to claim 1, comprising a couch driver that sets a position and an orientation of a couch bearing the patient laying thereon, based on the amount of deviation in position/orientation.

3. The patient position determination system according to claim 1, comprising a display device that displays an initial ROI image and the X-ray image or the DRR image, the initial ROI image indicating the region of interest estimated by the arithmetic processing apparatus, wherein the arithmetic processing apparatus corrects the region of interest estimated by the arithmetic processing apparatus, in accordance with a user's operation of correcting the region of interest, the user's operation being carried out when the initial ROI image and the X-ray image or the DRR image are displayed, and obtains the amount of deviation in position/orientation for the region of interest corrected.

4. The patient position determination system according to claim 1, comprising a display device that displays an ROI image indicating the region of interest, the X-ray image, the DRR image, and the amount of deviation in position/orientation, wherein the arithmetic processing apparatus corrects the region of interest in accordance with a user's operation of correcting the region of interest, the user's operation being carried out when the ROI image, the X-ray image, the DRR image, and the amount of deviation in position/orientation are displayed, and obtains the amount of deviation in position/orientation for the region of interest corrected.

5. The patient position determination system according to claim 3, wherein the display device displays a corrected ROI image indicating the region of interest corrected, the X-ray image, the DRR image, and the amount of deviation in position/orientation that is obtained based on the region of interest corrected, and wherein the arithmetic processing apparatus further corrects the region of interest in accordance with a user's operation of correcting the region of interest, the user's operation being carried out when the corrected ROI image, the X-ray image, the DRR image, and the amount of deviation in position/orientation that is obtained based on the region of interest corrected are displayed, and obtains the amount of deviation in position/orientation for the region of interest corrected.

6. The patient position determination system according to claim 5, comprising a storage device storing a dataset having the reference fluoroscopic image and the reference ROI image associated with each other, wherein the arithmetic processing apparatus judges whether or not to execute a storage process of storing the dataset in the storage device, according to a number of times of execution of a correction operation on the region of interest, and executes the storage process according to a result of the judgement, and wherein the storage process includes a process of associating the X-ray image or the DRR image and an image indicating the region of interest, the image being a source image from which the amount of deviation in position/orientation is obtained, with each other, as the reference fluoroscopic image and the reference ROI image, respectively, and defining the reference fluoroscopic image and the reference ROI image as the dataset.

7. The patient position determination system according to claim 1, comprising a storage device storing a dataset having the reference fluoroscopic image and the reference ROI image associated with each other, wherein the arithmetic processing apparatus associates the X-ray image or the DRR image and an image indicating the region of interest with each other, as the reference fluoroscopic image and the reference ROI image, respectively, and stores the reference fluoroscopic image and the reference ROI image as the dataset, in the storage device.

8. The patient position determination system according to claim 7, wherein the arithmetic processing apparatus additionally associates success/failure information with the reference fluoroscopic image and the reference ROI image, the success/failure information being information indicating whether the amount of deviation in position/orientation has been determined properly and being information corresponding to a user's operation, and stores the reference fluoroscopic image, the reference ROI image, and the success/failure information as the dataset, in the storage.

9. The patient position determination system according to claim 7, wherein the arithmetic processing apparatus additionally associates treatment site information with the reference fluoroscopic image and the reference ROI image, the treatment site information indicating a treatment site and being inputted by a user, and stores the reference fluoroscopic image, the reference ROI image, and the treatment site information as the dataset, in the storage device.

10. The patient position determination system according to claim 7, comprising a display device that displays an image indicating the region of interest, the X-ray image, the DRR image, and the amount of deviation in position/orientation, wherein the arithmetic processing apparatus stores the dataset in the storage device according to a user's operation that is carried out when the display device displays the image indicating the region of interest, the X-ray image, the DRR image, and the amount of deviation in position/orientation.

11. A patient position determination method comprising:

causing an X-ray imaging apparatus to obtain an X-ray image of a patient on a reference plane;

estimating a region of interest with respect to the X-ray image and to a DRR image, based on a parameter of a region estimation model and on the X-ray image or the DRR image created by virtually projecting a three-dimensional image of the patient obtained before radiotherapy onto the reference plane;

determining an amount of deviation in position/orientation between the patient and the three-dimensional image, based on the three-dimensional image, the X-ray image, and the region of interest; and calculating the parameter of the region estimation model using, as input data, a reference fluoroscopic image obtained before radiotherapy, and also using, as teacher data, the reference ROI image obtained with respect to the reference fluoroscopic image before radiotherapy.

12. A patient position determination program read by a position determination system including: an X-ray imaging apparatus that obtains an X-ray image of a patient on a reference plane; and an arithmetic processing apparatus, the patient position determination program causing the arithmetic processing apparatus to carry out the processes of:

estimating a region of interest with respect to the X-ray image and to a DRR image, based on a parameter of a region estimation model and on the X-ray image or the DRR image created by virtually projecting a three-dimensional image of the patient obtained before radiotherapy onto the reference plane; and determining an amount of deviation in position/orientation between the patient and the three-dimensional image, based on the three-dimensional image, the X-ray image, and the region of interest, wherein the parameter of the region estimation model is a parameter calculated by using, as input data, a reference fluoroscopic image obtained before radiotherapy, and also using, as teacher data, a reference ROI image obtained with respect to the reference fluoroscopic image before radiotherapy.

13. The patient position determination system according to claim 4, wherein the display device displays a corrected ROI image indicating the region of interest corrected, the X-ray image, the DRR image, and the amount of deviation in position/orientation that is obtained based on the region of interest corrected, and wherein the arithmetic processing apparatus further corrects the region of interest in accordance with a user's operation of correcting the region of interest, the user's operation being carried out when the corrected ROI image, the X-ray image, the DRR image, and the amount of deviation in position/orientation that is obtained based on the region of interest corrected are displayed, and obtains the amount of deviation in position/orientation for the region of interest corrected.

14. The patient position determination system according to claim 13, comprising a storage device storing a dataset having the reference fluoroscopic image and the reference ROI image associated with each other, wherein the arithmetic processing apparatus judges whether or not to execute a storage process of storing the dataset in the storage device, according to a number of times of execution of a correction operation on the region of interest, and executes the storage process according to a result of the judgement, and wherein the storage process includes a process of associating the X-ray image or the DRR image and an image indicating the region of interest, the image being a source image from which the amount of deviation in position/orientation is obtained, with each other, as the reference fluoroscopic image and the reference ROI image, respectively, and defining the reference fluoroscopic image and the reference ROI image as the dataset.

* * * * *